US007048689B2

(12) United States Patent
Ogawa

(10) Patent No.: US 7,048,689 B2
(45) Date of Patent: *May 23, 2006

(54) ULTRASONIC RECEIVING APPARATUS AND ULTRASONIC RECEIVING METHOD

(75) Inventor: Eiji Ogawa, Kaisei-machi (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 230 days.

This patent is subject to a terminal disclaimer.

(21) Appl. No.: 10/649,610

(22) Filed: Aug. 28, 2003

(65) Prior Publication Data

US 2004/0092808 A1    May 13, 2004

(30) Foreign Application Priority Data

Aug. 30, 2002    (JP) .............................. 2002-252397

(51) Int. Cl.
*A61B 8/00* (2006.01)
(52) U.S. Cl. .................. 600/443; 356/479; 73/603; 359/1
(58) Field of Classification Search ................ 600/437, 600/443, 447; 73/603, 606, 608, 597; 367/138, 367/149; 356/477, 479, 502; 348/493, 769; 359/1, 7, 30, 32; 342/179
See application file for complete search history.

(56) References Cited

U.S. PATENT DOCUMENTS 6,709,393 B1 *    3/2004    Ogawa ........................ 600/443

6,881,189 B1 *    4/2005    Ogawa ........................ 600/459

OTHER PUBLICATIONS

Takahashi et al. Underwater Acoustic Sensor with Fiber Bragg Grating Optical Review vol. 4, No. 6 (1997) pp. 691-694.
Uno et al. Fabrication and Performance of a Fiber Optic Micro-Probe for Megahertz Ultrasonic Field Measurements T. IEE Japan, vol. 118-E, No. 11, (1998) pp. 487-492.
Beard et al. Transduction Mechanisms of the Fabry-Perot Polymer Film Sensing Concept for Wideband Ultrasound Detection pp. 1575-1583.

* cited by examiner

*Primary Examiner*—Francis J. Jaworski
(74) *Attorney, Agent, or Firm*—Sughrue Mion, PLLC

(57) ABSTRACT

To reduce the cost while maintaining the real time environment in receiving ultrasonic waves in an ultrasonic receiving apparatus which is capable of reducing changes in detection sensitivity due to environmental changes in the ultrasonic detecting element. The ultrasonic receiving apparatus comprises a light source for generating broadband light, an ultrasonic detecting element including an ultrasonic sensing portion that expands and contracts in response to a received ultrasonic wave and has optical reflectance that changes in accordance with expansion and contraction thereby performing intensity modulation on the light, spectrum-separating means for spectrum-separating the light, first photo-detecting means having a plurality of photoelectric conversion elements for detecting the light for plural wavelength components, and second photo-detecting means for detecting a selected wavelength component included in the light on the basis of a detection result of the first photo-detecting means.

7 Claims, 12 Drawing Sheets

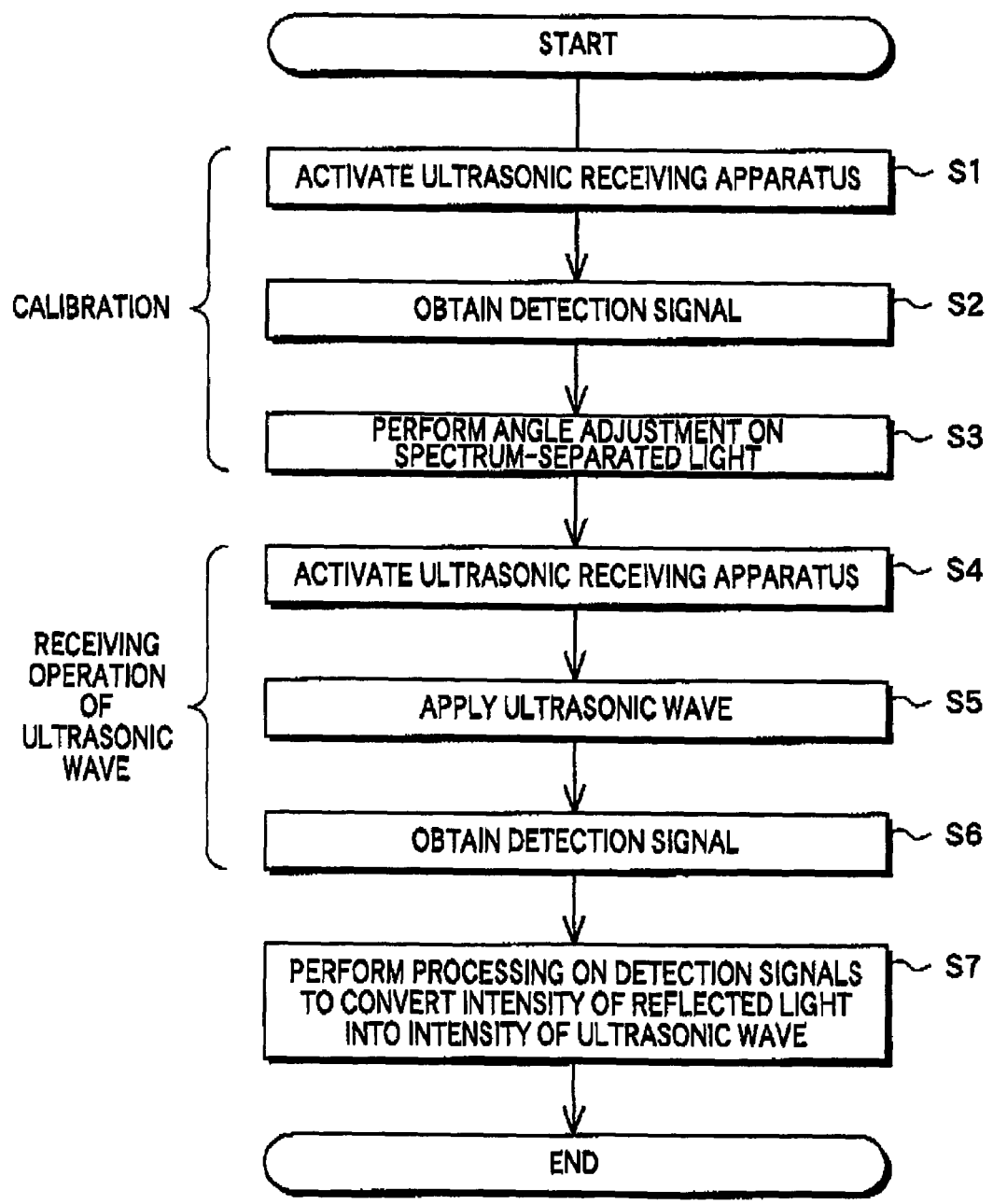

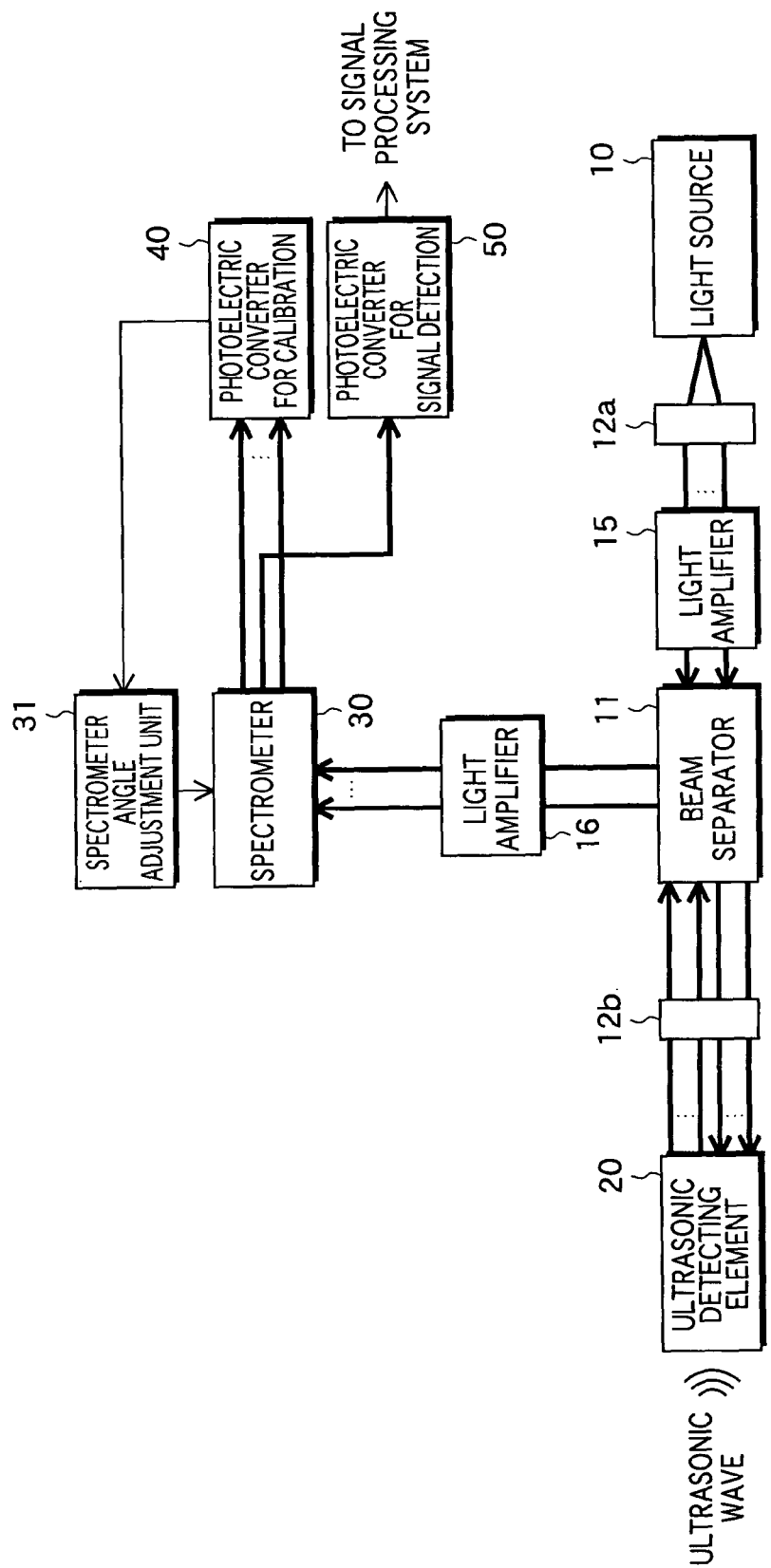

ULTRASONIC RECEIVING APPARATUS AND ULTRASONIC RECEIVING METHOD

BACKGROUND OF THE INVENTION

1. Field of the Invention

The present invention relates to an ultrasonic receiving apparatus to be used for obtaining ultrasonic images by receiving ultrasonic waves.

2. Description of a Related Art

Recently, in order to obtain high quality three-dimensional images using ultrasonic waves, development of a two-dimensional sensor capable of obtaining two-dimensional images without mechanically shifting a sensor array is proceeding.

Conventionally, as an element (vibrator) used for transmitting and receiving ultrasonic waves, a piezoelectric element that includes piezoelectric ceramic represented by PZT (Pb (lead) zirconate titanate) or macromolecule piezoelectric material represented by PVDF (polyvinylidene difluoride) has been generally used. However, in the case where the two-dimensional array is fabricated by using these elements, since micro-processing on elements and wiring to a large number of micro-elements are required, it is difficult to achieve further miniaturization and integration of elements. Even though the difficulties could be overcome, such problems still remain that crosstalk between elements increases, electrodes of microelements become easily broken, and SN-ratio becomes lower due to increase of electric impedance caused by micro-wirings. Consequently, it is difficult to apply the two-dimensional sensor array using PZT or PVDF in practice.

In order to avoid such problems, also a photo-detection type ultrasonic sensor is under study in which a received ultrasonic wave signal is converted into an optical signal and then detected. As the photo-detection type ultrasonic sensor, a sensor in which a fiber Bragg grating (abbreviated as FBG) is used (for example, TAKAHASHI et al. (National Defense Academy) "Underwater Acoustic Sensor with Fiber Bragg Grating", OPTICAL REVIEW Vol. 4, No. 6 (1997), pp. 691–694), and a sensor in which a Fabry-Perot resonator (abbreviated as FPR) structure is used (for example, UNO et al. (Tokyo Institute of Technology) "Fabrication and Performance of a Fiber Optic Micro-Probe for Megahertz Ultrasonic Field Measurement", T.IEE Japan, Vol. 118-E, No. 11, 1998, pp. 487–492) are reported. Fabricating a two-dimensional sensor array by using such ultrasonic sensor provides the advantages that electrical wiring to a large number of microelements is not required and good sensitivity can be obtained.

Further, as a photo-detection type ultrasonic sensor having a two-dimensional detection surface, it is also proposed that a polymer film having a Fabry-Perot structure is used for detecting ultrasonic waves (Beard et al. (University College London) "Transduction Mechanisms of the Fabry-Perot Polymer Film Sensing Concept for Wideband Ultrasound Detection", IEEE TRANSACTIONS ON ULTRASONICS, FERROELECTRICS, AND FREQUENCY CONTROL, VOL. 46, NO. 6, NOVEMBER 1999, pp. 1575–1582). In the film-like ultrasonic sensor, since processing on a large number of microelements is not required, the cost can be reduced. The photo-detection type ultrasonic sensor utilizes an ultrasonic detecting element having optical reflectance characteristics that change by receiving ultrasonic waves.

However, in such ultrasonic detecting element, the detection sensitivity widely varies since the optical reflection characteristics change due to changes in temperature and humidity. Further, in the ultrasonic detecting element having a two-dimensional detection surface, the detection sensitivity varies since the optical reflection characteristics differ depending on the respective positions on the detection surface. As described above, the problem in practical use of the photo-detection type ultrasonic sensor is how to control changes in detection sensitivity caused by environmental factors such as temperature and structural factors. For this purpose, a conceivable solution is, for example, to adjust the wavelength of the light outputted from the light source to the point where the sensitivity of the ultrasonic detecting element is high. However, it is difficult to tune the wavelength of the light outputted from the light source because the reflection characteristics change very steeply. Another conceivable solution is to allow broadband light to enter the ultrasonic detecting elements having different reflection characteristics depending on the positions and to separate the reflected light by filtering it. In this case, however, there are problems that the constitution of the ultrasonic detecting element becomes complicated, and the cost rises. Yet another conceivable solution is to vary the reflection characteristics in respective plural detection areas of the ultrasonic detecting element. Also in this case, however, the constitution of the ultrasonic detecting element becomes complicated and the cost rises.

SUMMARY OF THE INVENTION

The present invention has been achieved in view of the above-described problems. An object of the present invention is, in an ultrasonic receiving apparatus using a photo-detection technique, to reduce changes in the detection sensitivity to ultrasonic waves caused by environmental changes such as changes in temperature and variations in the detection sensitivity depending on the positions in the ultrasonic detecting element, and to cut down on costs while maintaining real time environment in receiving ultrasonic waves.

In order to solve the above-described problems, an ultrasonic receiving apparatus according to one aspect of the present invention comprises: a light source for generating broadband light; an ultrasonic detecting element including an ultrasonic sensing portion that expands and contracts in response to a received ultrasonic wave and has optical reflectance that changes in accordance with expansion and contraction thereby performing intensity modulation on the light generated by the light source; spectrum-separating means for spectrum-separating the light intensity-modulated by the ultrasonic detecting element; first photo-detecting means having a plurality of photoelectric conversion elements for detecting the light spectrum-separated by the spectrum-separating means for plural wavelength components, respectively; and second photo-detecting means for detecting a selected wavelength component included in the light spectrum-separated by the spectrum-separating means on the basis of a detection result of the first photo-detecting means.

According to the present invention, the reflection characteristics of the ultrasonic detecting element can be obtained by spectrum-separating the light intensity-modulated by the ultrasonic detecting element and allowing the light to enter the different photoelectric conversion elements. Further, by selecting the wavelength component, which is used when detecting the ultrasonic wave, from the spectrum-separated light of the broadband light on the basis of the reflection characteristics, detection signals with high sensitivity can be obtained. Furthermore, by using different elements when obtaining the reflection characteristics of the ultrasonic detecting element and when receiving ultrasonic waves, suitable photoelectric conversion elements and processing circuits can be applied for the respective purposes, thereby the cost can be reduced as the whole apparatus while maintaining real time environment in receiving ultrasonic waves. Note that, in this application, the "reflection characteristics" means the relationship between wavelength and reflection intensity of the light.

BRIEF DESCRIPTION OF THE DRAWINGS

FIG. 6 is a flowchart showing an operation of the ultrasonic receiving apparatus according to the first embodiment of the present invention;

FIG. 11 is a block diagram showing a modification of the ultrasonic receiving apparatus according to the first embodiment of the present invention;

DESCRIPTION OF THE PREFERRED EMBODIMENTS

Figure 1:
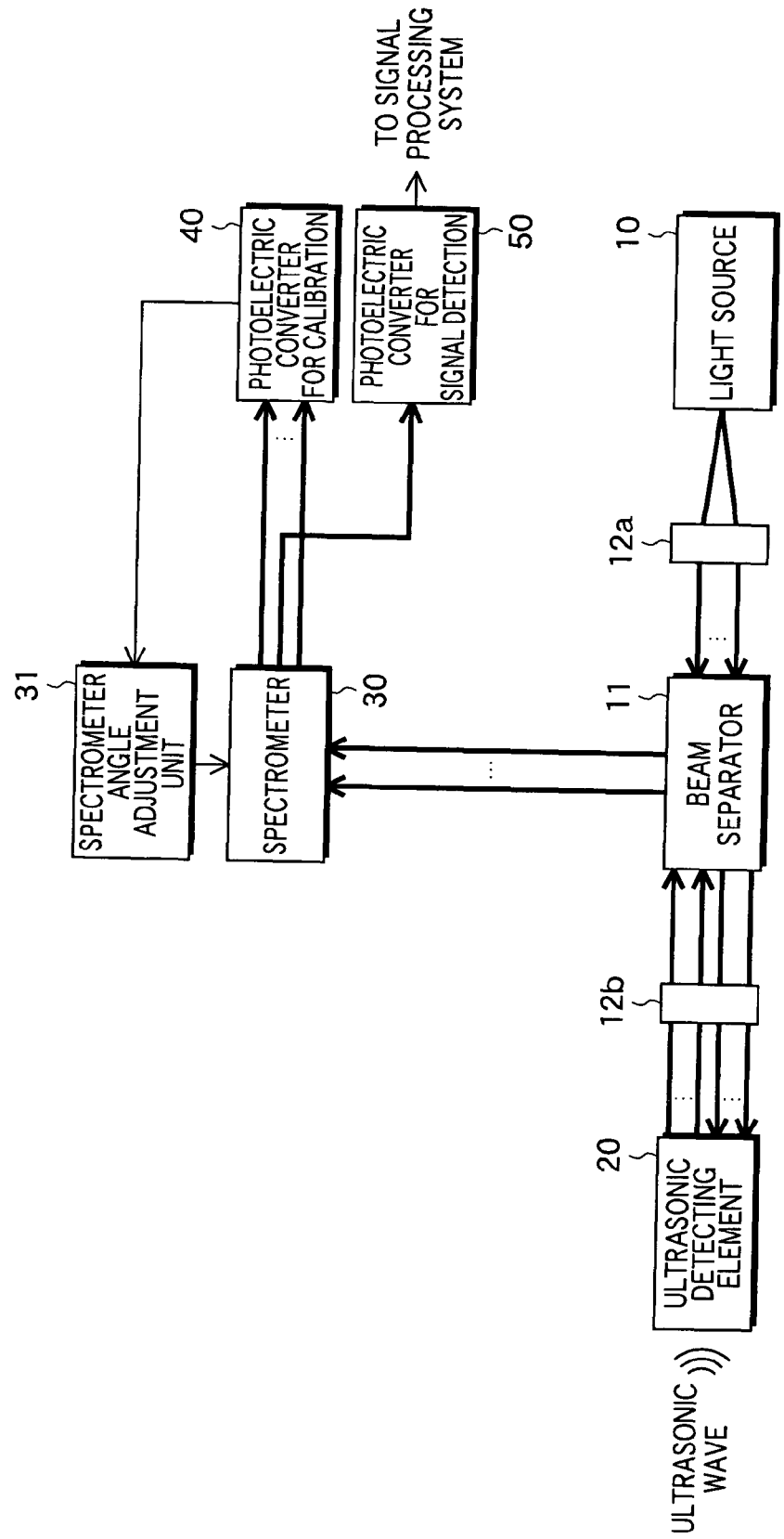
FIG. 1 is a block diagram showing a constitution of an ultrasonic receiving apparatus according to a first embodiment of the present invention.

Hereinafter, embodiments of the present invention will be described in detail by referring to the drawings. The same component elements will be given with the same reference numerals and the descriptions thereof will be omitted.

Figure 2:
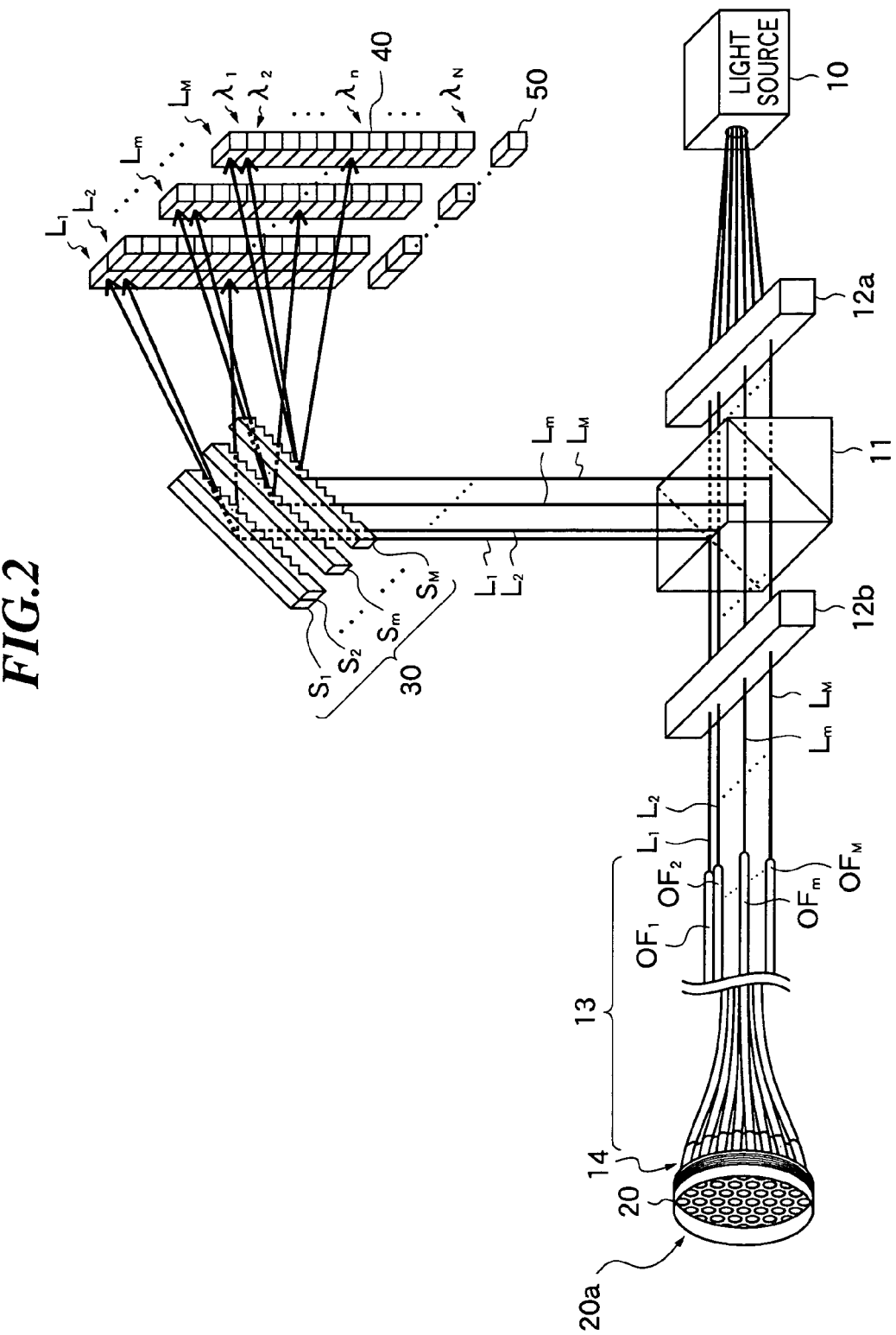
FIG. 2 is a diagram showing an optical system included in the ultrasonic receiving apparatus shown in FIG. 1.

FIG. 1 is a block diagram showing an ultrasonic receiving apparatus according to a first embodiment of the present invention. FIG. 2 is a diagram showing an optical system included in the ultrasonic receiving apparatus shown in FIG. 1. As shown in FIG. 1, this ultrasonic receiving apparatus has a light source 10, a beam separator 11, collimator lenses 12a and 12b, an ultrasonic detecting element 20, a spectrometer 30, a spectrometer angle adjustment unit 31, a photoelectric converter 40 for calibration, and a photoelectric converter 50 for signal detection.

The light source 10 generates broadband light used for detecting ultrasonic waves. As the light source 10, it is desirable to use one having a bandwidth that can cover a wider range over an inclined band in the reflection characteristics of the ultrasonic detecting element 20. As such light source, an LED (light emitting diode), an SLD (super luminescent diode), an ASE (amplified spontaneous emission) light source, a broadband light source such as an LD (Laser Diode) having a relatively large line width can be used.

The collimator lens 12a is disposed between the light source 10 and the beam separator 11. The collimator lens 12a collimates the light emitted from the light source 10 and allows the light enter the beam separator 11.

The beam separator 11 guides the light emitted from the light source 10 and passing through the collimator lens 12a to the ultrasonic detecting element 20, and the light returning by being reflected from the ultrasonic detecting element 20 to the spectrometer 30. The beam separator 11 is constituted by, for example, a half mirror, a light circulator or a polarizing beam splitter. In the embodiment, as shown in FIG. 2, a half mirror is used as the beam separator 11. The half mirror allows the incident light to transmit in a direction opposite to the incident direction, and reflects the light returning from the direction opposite to the incident direction, in a direction substantially at an angle of 90° with the incident direction.

The ultrasonic detecting element 20 is a two-dimensional sensor for detecting ultrasonic waves by the photo-detection technique. In this embodiment, a multi-layered film sensor having a two-dimensional ultrasonic receiving surface 20a is used as the ultrasonic detecting element 20. The ultrasonic detecting element 20 has a two-dimensional receiving surface 20a that is distorted by a propagating ultrasonic wave, and an ultrasonic sensing portion that expands and contracts in response to the ultrasonic wave received by the receiving surface 20a. The ultrasonic detecting element 20 performs intensity modulation on the light, which has been emitted from the light source 10 and passed through the beam separator 11 and entered the element, on the basis of the ultrasonic waves received in respective positions on the ultrasonic wave receiving surface 20a, and reflects it. The structure and operation of the ultrasonic detecting element 20 will be described later in detail.

Here, as shown in FIG. 2, the light having passed through the beam separator 11 enters the ultrasonic detecting element 20 via an optical transmission path 13. As the optical transmission path 13, a bundle fiber in which a large number of optical fibers (for example, 1,024 fibers) are bundled etc. is used. FIG. 2 shows optical fibers $OF_1$–$OF_M$ arranged in a line. As shown in FIG. 1, the large number of optical fibers are bundled into a configuration in accordance with a form of a receiving surface (a circular configuration, for example) on the ultrasonic detecting element side (on the left side in the drawing), and arranged in a line on the beam separator 11 side (on the right side in the drawing). Alternatively, plural rows of optical fibers arranged in a line may be stacked one another.

The front end of the optical transmission path 13 is connected to the ultrasonic detecting element 20 with the optical axes thereof aligned with each other via a collimating portion 14. As the collimating portion 14, for example, a collimator lens array in which collimator lenses are arrayed is used. The constitution of the optical transmission path 13 and the collimating portion 14 will be described later in detail.

The collimator lens 12b is disposed between the beam separator 11 and the optical transmission path 13. The collimator lens 12b collimates the light reflected by the ultrasonic detecting element and outputted from the optical fibers $OF_1$–$OF_M$, and allows the light enter the beam separator 11.

The spectrometer 30 includes a plurality of spectrum-separating elements $S_1$–$S_M$ constituted by a diffraction grating, a prism, or an AWG (array waveguide grating), etc. These spectrum-separating elements $S_1$–$S_M$ are disposed so that light beams $L_1$–$L_M$ outputted from the optical fibers $OF_1$–$OF_M$ may enter the elements, respectively. The respective spectrum-separating elements spectrum-separate the entering light beams and output them in directions that differ from each other according to the wavelength.

Figure 3:
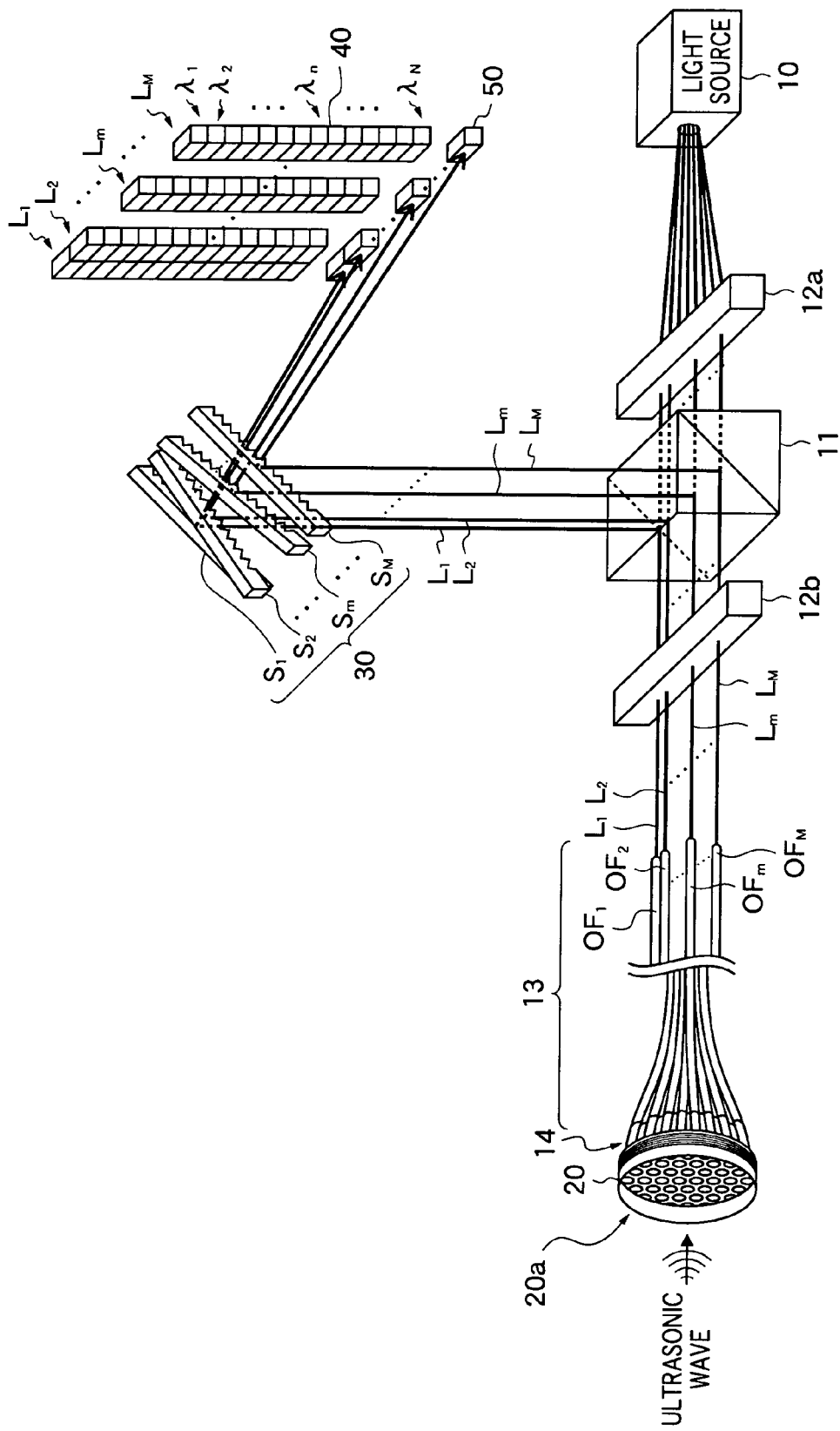
FIG. 3 is a diagram showing a state in which an angle of a spectrum-separating element has been adjusted in the optical system shown in FIG. 2.

The spectrometer angle adjustment unit 31 shown in FIG. 1 adjusts the optical system so that a certain wavelength component of the broadband light reflected by the ultrasonic detecting element 20 may be subjected to signal detection. That is, the spectrometer angle adjustment unit 31 adjusts angles of the plural spectrum-separating elements $S_1$–$S_M$ on the basis of the detection result of the photoelectric converter 40 for calibration, so that the spectrum-separated light having a certain wavelength may enter the photoelectric converter 50 for signal detection. FIG. 3 shows a state in which the spectrum-separated light having the wavelength enters the photoelectric converter 50 for signal detection under the control of the spectrometer angle adjustment unit 31.

The photoelectric converter 40 for calibration is a photo detector to be used in calibration performed prior to receiving ultrasonic waves. Here, the calibration indicates the operation for measuring the reflection characteristics of the ultrasonic detecting element 20 at given times and selecting a wavelength component to be adopted as a detection signal. As the photoelectric converter 40 for calibration, a two-dimensional sensor array is used in which a plurality of photoelectric conversion elements are arranged in a two-dimensional manner and the incident light can be detected by being divided in respective positions. As such two-dimensional sensor array, a PDA (photo diode array) or a MOS-type sensor can be used, for example. Alternatively, a programmable two-dimensional sensor such as a CCD (charge coupled device) may be used. Since the photoelectric converter 40 for calibration is not used when receiving ultrasonic waves, one having relatively low-speed processing capability can also be applied.

The photoelectric conversion elements of the photoelectric converter 40 for calibration are disposed so that the spectrum-separated light spectrum-separated by the spectrum-separating elements $S_1$–$S_M$ may enter the first column through the Mth column, respectively. Further, in the respective columns of the photoelectric converter 40 for calibration, the photoelectric conversion elements are disposed so that the light spectrum-separated by the corresponding spectrum-separating elements may enter the first row through the Nth row according to wavelengths. By disposing the photoelectric conversion elements as above, for example, the signal detected from the photoelectric conversion element located in the "n"th row and the "m"th column of the photoelectric converter 40 for calibration is determined as the component having the wavelength $\lambda_n$ included in the light beam $L_m$ outputted from the optical fiber $OF_m$.

The photoelectric converter 50 for signal detection is a photo detector to be used when receiving ultrasonic waves. As the photoelectric converter 50 for signal detection, for example, a PDA in which a plurality of PDs are arranged in a one-dimensional manner is used. It is desirable that the photoelectric converter 50 for signal detection has high-speed signal processing capability in order to receive ultrasonic wave signals in real time. As shown in FIG. 2, the plural photoelectric conversion elements included in the photoelectric converter 50 for signal detection are disposed in correspondence to plural columns of the photoelectric converter 40 for calibration, respectively. Further, as shown in FIG. 3, when receiving ultrasonic waves, the angles of the detecting elements $S_1$–$S_M$ are adjusted under the control of the spectrometer angle adjustment unit 31, and the spectrum-separated light selected by the calibration enters the corresponding photoelectric conversion elements of the photoelectric converter 50 for signal detection with respect to the respective light beams $L_1$–$L_M$.

Furthermore, a signal processing system is provided in a subsequent stage of the photoelectric converter 50 for signal detection, and changes in intensity of the signal detected by the photoelectric converter 50 for signal detection will be converted into a signal representing an amplitude of the ultrasonic wave received by the ultrasonic detecting element.

Figure 4:
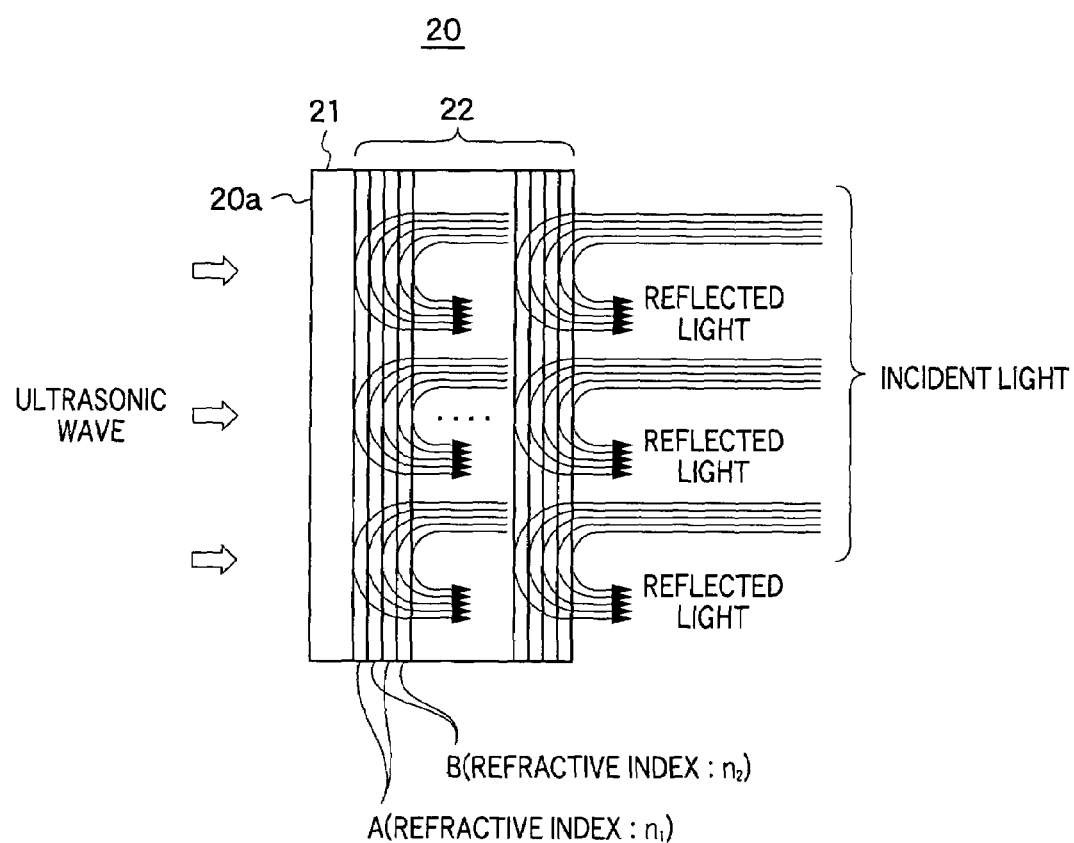
FIG. 4 is an explanatory diagram of a principle of detecting ultrasonic waves in the ultrasonic detecting element shown in FIG. 2.

Next, referring to FIG. 4, the structure of the ultrasonic detecting element 20 and the detecting principle of an ultrasonic wave will be described in detail. The ultrasonic detecting element 20 is a multi-layered sensor including a substrate 21 and a multi-layered film 22 laminated on the substrate. This multi-layered film 22 constitutes a Bragg grating structure and serves as an ultrasonic sensing portion.

The substrate 21 is a film-like substrate which is distorted by receiving an ultrasonic wave and has an area equal to or larger than a circle of approximately 2 cm in diameter, for example. The multi-layered film 22 having the Bragg grating structure is formed on the substrate 21 by alternately laminating two kinds of material layers that have different refractive indexes. FIG. 4 shows material layers A having a refractive index $n_1$ and material layers B having a refractive index $n_2$.

Assuming that a pitch (distance) of a periodical structure of the multi-layered film 22 is "d" and that the wavelength of the incident light is "λ", the Bragg's reflection condition is expressed by the following formula.

$$2d \cdot \sin\theta = m\lambda \quad (1)$$

Herein, "θ" denotes an incident angle measured from the incidence plane, and "m" is an arbitrary integer number. Assuming that $\theta = \pi/2$, the following formula is held.

$$2d = m\lambda \quad (2)$$

The Bragg grating selectively reflects light having a specific wavelength, which meets the Bragg's reflection conditions, and transmits light having other wavelengths.

When an ultrasonic wave is propagated to the ultrasonic detecting element 20, the detecting element 20 is distorted with the propagation of the ultrasonic wave, and the pitch "d" of the periodical structure changes in the respective positions of the multi-layered film 22. Accordingly, the wavelength "λ" of the selectively reflected light changes. In the reflection characteristics of the Bragg grating, there is an inclined band, where the optical reflectance changes, in the vicinity of a wavelength at which the optical reflectance is the highest (i.e., an optical transmittance is lowest). While allowing the light having a center wavelength within the range of the inclined band to enter the multi-layered film 22, an ultrasonic wave is applied. Then, changes in intensity of the reflected light (or transmitted light) according to the intensity of the ultrasonic wave in the respective positions on the receiving surface can be observed. The two-dimensional intensity distribution information of the ultrasonic wave can be obtained by converting the changes in the intensity of the light into the intensity of the ultrasonic wave.

As the material of the substrate 21, optical glass such as silica glass ($SiO_2$), BK7 (a product of SCHOTT), etc. can be used. As the substances to be used for the material layers A and B, a combination of substances having refractive indexes different by 10% or more from each other is desirable. For example, a combination of $SiO_2$ and titanium oxide ($Ti_2O_3$), a combination of $SiO_2$ and tantalum oxide ($Ta_2O_5$), etc. can be used. The material layers A and B are formed on the substrate 21 by a method such as vacuum deposition or sputtering.

By the way, in order to reduce the multiple reflection of an ultrasonic wave, it is effective to elongate the distance through which the ultrasonic wave propagates. Not a little of the ultrasonic wave attenuates during propagation. The longer propagation distance results in a larger attenuation amount. Therefore, by ensuring a sufficient propagation distance, the ultrasonic wave can be satisfactorily attenuated while the ultrasonic wave having propagated to one end is reflected at the other end and returns to the one end. For this purpose, in the embodiment, an optical fiber is used as the optical transmission path, and the received ultrasonic wave is allowed to propagate through the optical fiber. That is, the optical transmission path is made to have both a function of allowing the light to pass through it and a function as the backing portion of attenuating the ultrasonic wave as well.

Figure 5:
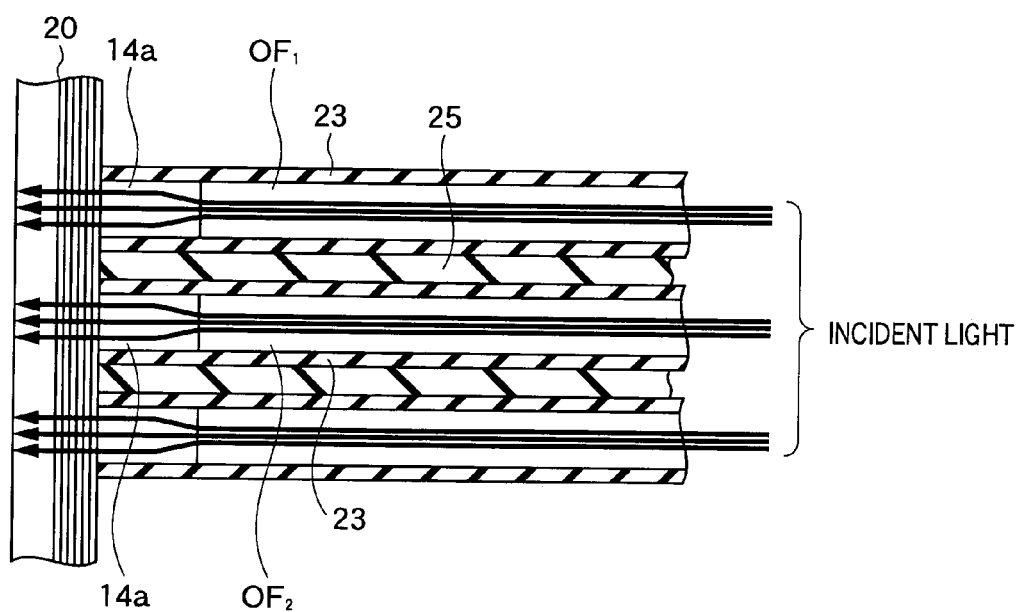
FIG. 5 is an expanded sectional view showing the ultrasonic detecting element, a collimating portion, and a connecting portion of an optical transmission path shown in FIG. 2.

FIG. 5 is an expanded sectional view showing a part of the optical transmission path 13, the collimating portion 14, and the ultrasonic detecting element 20 shown in FIG. 2. As shown in FIG. 5, the optical fibers $OF_1$, $OF_2$, . . . included in the optical transmission path (bundle fiber) 13 are connected to plural collimator lenses 14a included in the collimating portion (collimator lens array) 14 with optical axes thereof being aligned respectively, and are disposed in a two-dimensional manner and connected to the ultrasonic detecting element 20. The optical fibers $OF_1$, $OF_2$, . . . are bundled by using an adhesive agent 24.

The optical fibers $OF_1$, $OF_2$, . . . are, for example, single mode or multi mode fibers of approximately 2 m in length and are covered with a member (covering material 23) including a resinous material and having a low viscosity. In order to attenuate the ultrasonic wave during the propagation through the optical fiber, the length of 2 m is effective, and propagation energy loss of the ultrasonic wave is further increased by covering the optical fiber with the above member, resulting in earlier ultrasonic wave attenuation.

Here, the light transmitted in the optical fibers $OF_1$, $OF_2$, . . . is diffracted when the light is outputted from the optical fibers. Accordingly, in the case where the optical fibers $OF_1$, $OF_2$, . . . are connected directly to the ultrasonic detecting element 20, the light is diffused and satisfactory interference is not produced within the ultrasonic detecting element. As a result, the detection sensitivity of the ultrasonic detecting element becomes significantly lower. In order to avoid this phenomenon, the collimator lenses 14a are connected to one ends of the optical fibers $OF_1$, $OF_2$, . . . , respectively, to prevent the outputted light from being diffused.

As the collimator lens 14a, a gradient index lens (hereinafter, abbreviated to GRIN lens) can be used. The GRIN lens is known as, for example, the product name of Selfoc (registered trademark of NIPPON SHEET GLASS CO., LTD.) lens. The GRIN lens is a gradient refractive index type lens having a refractive index that differs depending on positions, and the optical characteristics thereof change by changing its length. For example, when the GRIN lens has a length of ¼ of a distance between an object and an image (a pitch under which the light focuses electing image), the incident light is outputted as collimated light.

In the embodiment, Selfoc lens array NA0.46 (a product of NIPPON SHEET GLASS CO., LTD.), in which a number of Selfoc lenses are disposed, is used in a length of 0.25L (L: a distance between an object and an image), and the respective Selfoc lenses as the collimator lenses 14a are connected to the optical fibers.

As shown in FIG. 5, the collimator lenses 14a may be covered with the covering material 23 in order to allow the ultrasonic wave to attenuate earlier as in the case of the optical fibers $OF_1$, $OF_2$ . . . .

The optical fiber and the collimator lens, or, the collimator lens and the ultrasonic detecting element are connected by means of a fusion bond or an adhesive agent. In the case where an adhesive agent is used, it is desirable to use a resinous adhesive agent including epoxy series adhesives. Because such adhesive agent has acoustic impedance close to that of the members of the optical fiber and the collimator lens or the substrate of the ultrasonic detecting element, and the ultrasonic wave can be prevented from being reflected at boundaries of the respective members during the propagation. It is also desirable to use the resinous adhesive agent including epoxy series adhesives as the adhesive agent 24 for bundling the plural optical fibers. Because the ultrasonic wave can be attenuated, cross talk of the ultrasonic wave between the neighboring optical fibers can be prevented, and the flexibility as a cable can be maintained. In this embodiment, STYCAST (a product of Emerson & Cuming) is used as the adhesive agent.

Next, the operation of the ultrasonic receiving apparatus according to this embodiment will be described referring to FIGS. 1–3, 6, and 7A–7C. FIG. 6 is a flowchart showing the operation of the ultrasonic receiving apparatus according to this embodiment.

First, calibration is performed prior to receiving an ultrasonic wave. Here, the ultrasonic detecting element is highly sensitive to an ambient environment such as temperature and humidity, and the optical reflection characteristics thereof are changeable. For example, a center wavelength of the light reflected from the ultrasonic detecting element using the Bragg grating changes at a rate of 0.01 nm/° C. Further, in the ultrasonic detecting element having a two-dimensional detection surface, there is structural unevenness in respective micro-areas on the surface. In order to reduce changes in the sensitivity caused by those environmental or structural factors, the calibration is performed in advance. The calibration may be performed as needed after starting to receive an ultrasonic wave.

At step S1, the ultrasonic receiving apparatus is activated. Accordingly, the broadband light having spectrum characteristics shown in FIG. 7A, for example, is outputted from the light source 10. As shown in FIG. 2, the light outputted from the light source 10 passes through the collimator lens 12a, the beam separator 11, and the collimator lens 12b, and enters the optical fibers $OF_1$–$OF_M$ arranged in a line. The light transmitted through the respective optical fibers enters the respective micro-areas of the ultrasonic detecting element 20, and the light reflected in correspondence to the reflection characteristics of the respective micro-areas is outputted from the optical fibers. The light beams $L_1$–$L_M$ outputted from the optical fibers $OF_1$–$OF_M$ pass through the collimator lens 12b again, are reflected by the beam separator 11, and enter the spectrometer 30. The light beams $L_1$–$L_M$ are simultaneously spectrum-separated in the spectrum-separating elements $S_1$–$S_M$ included in the spectrometer 30, and the respective pieces of spectrum-separated light enter the plural photoelectric conversion elements included in the respective columns of the photoelectric converter 40 for calibration in accordance with wavelengths.

Accordingly, at step S2, the detection signals of the photoelectric conversion elements corresponding to wavelengths $\lambda_1$–$\lambda_N$ are obtained from the respective columns of the photoelectric converter 40 for calibration, which columns correspond to the light beams $L_1$–$L_M$. As shown in FIG. 1, this detection result is inputted to the spectrometer angle adjustment unit 31.

Figure 7A:
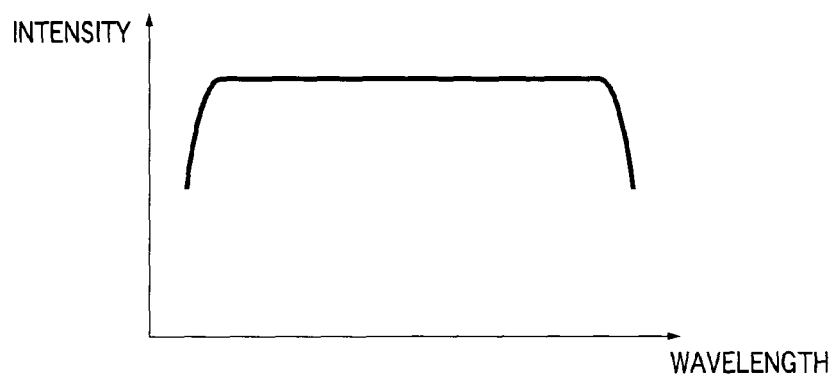
FIGS. 7A–7C are explanatory diagrams of the operation of the ultrasonic receiving apparatus according to the first embodiment of the present invention.
Figure 7B:
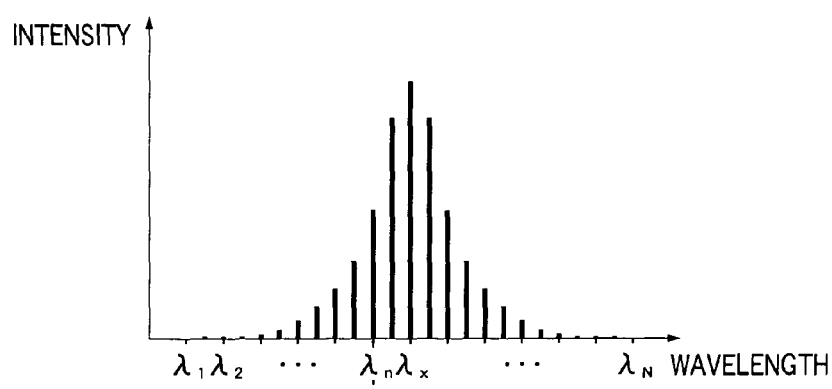

FIG. 7B is a graph obtained on the basis of the detection signal outputted from the plural photoelectric conversion elements included in the "m"th column of the photoelectric converter 40 for calibration. That is, this graph shows a spectral distribution of the light beam $L_m$ that has passed through the optical fiber $OF_m$ and is reflected from the micro-areas of the corresponding ultrasonic detecting element. As shown in FIG. 7B, the light beam $L_m$ has the highest intensity at the wavelength $\lambda_x$, where the light beam $L_m$ is selectively reflected under the Bragg's reflection condition.

Figure 7C:
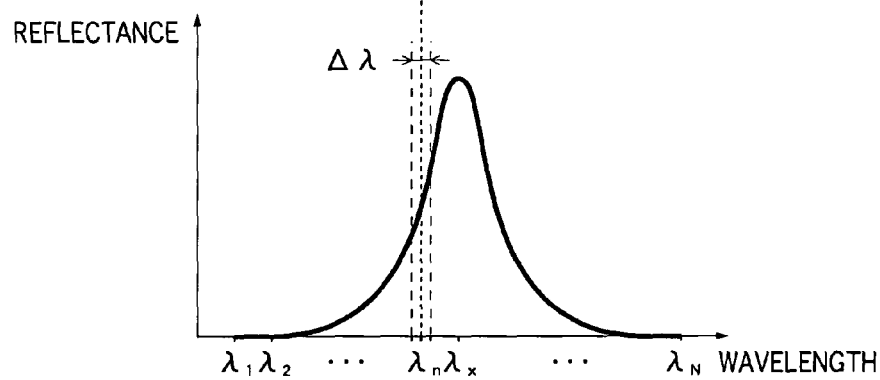

FIG. 7C shows the reflection characteristics of the Bragg grating in the micro-areas of the ultrasonic detecting element corresponding to the light beam $L_m$. As described above, in the reflection characteristics of the Bragg grating, there is an inclined band $\Delta\lambda$ where the reflectance changes steeply in the vicinity of the wavelength $\lambda_x$ at which the reflectance is the highest (the transmittance is lowest). When observing the changes in the Bragg grating structure by applying an ultrasonic wave, large changes in intensity are observed in the detection area corresponding to the inclined band $\Delta\lambda$. The center wavelength is shown as $\lambda_n$ in FIGS. 7B and 7C.

That is, with respect to the micro-areas of the ultrasonic detecting element corresponding to the light beam $L_m$, the light in a spectrum-separated range having the center wavelength $\lambda_n$ shows largest changes in intensity. Therefore, it is possible to obtain the highest detection sensitivity by using the light in the detection area as a detection signal when receiving the ultrasonic wave.

At step S3, the spectrometer angle adjustment unit 31 adjusts the angles of spectrum-separating elements $S_1$–$S_M$ so that the spectrum-separated light having a wavelength, which is selected on the basis of the pre-detected result in the calibration, may enter the photoelectric converter 50 for signal detection with respect to each of the light beams $L_1$–$L_M$. As shown in FIG. 3, for example, with respect to the light beam $L_m$, the angle of the spectrum-separating element $S_m$ is adjusted so that the spectrum-separated light having the center wavelength $\lambda_n$ may enter the "m"th photoelectric conversion element of the photoelectric converter 50 for signal detection. Thereby, with respect to the light beams $L_1$–$L_M$ outputted from the optical fibers $OF_1$–$OF_M$, the light beams having center wavelengths in the inclined band of the reflection characteristics will enter the corresponding photoelectric conversion elements of the photoelectric converter 50 for signal detection, respectively.

Next, the receiving operation of an ultrasonic wave will be performed.

At step S4, the ultrasonic receiving apparatus is activated. Accordingly, the broadband light outputted from the light source passes through the optical fibers $OF_1$–$OF_M$ and enters the micro-areas of the ultrasonic detecting element 20. The light beams $L_1$–$L_M$ reflected from the respective micro-areas are spectrum-separated in the spectrometer 30 and, for each of the light beams $L_1$–$L_M$, the spectrum-separated light having the selected wavelength enters the photoelectric converter 50 for signal detection.

In this state, the ultrasonic detecting element 20 is allowed to receive an ultrasonic wave (step S5). Thereby, the pitch of the periodical structure changes in each micro-area of the ultrasonic detecting element 20, and the detection signals outputted from the respective photoelectric conversion elements included in the photoelectric converter 50 for signal detection show large changes in intensity.

Next, at step S6, the detection signals outputted from the plural photoelectric conversion elements included in the photoelectric converter 50 for signal detection are obtained. Further, processing on these detection signals are performed so that the changes in the intensity of the reflected light are converted into the intensity of the ultrasonic wave step S7. Thereby, the intensity of the ultrasonic wave applied to the respective micro-areas of the ultrasonic detecting element is measured in a two-dimensional way.

Figure 8:
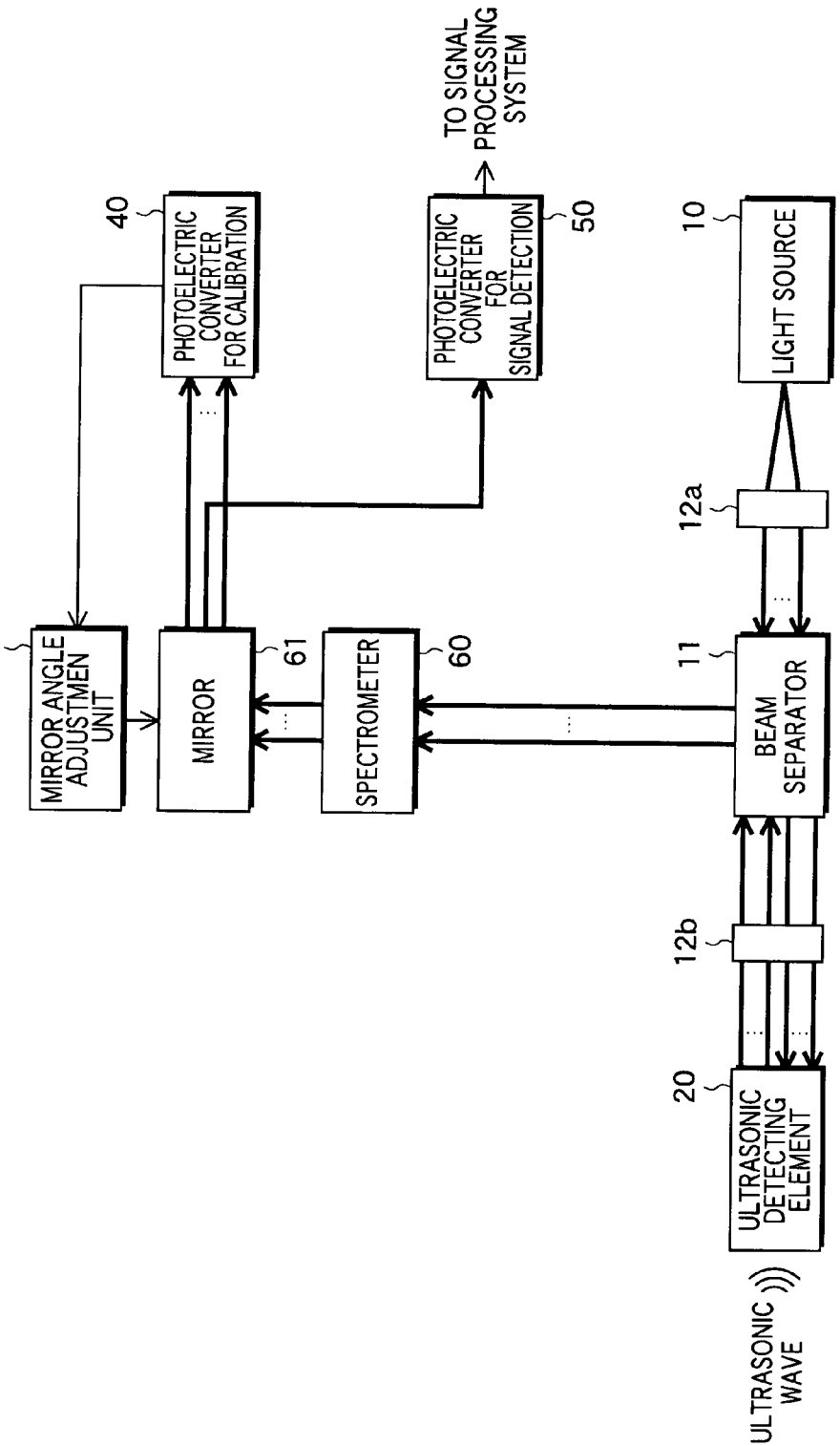
FIG. 8 is a block diagram showing a constitution of an ultrasonic receiving apparatus according to a second embodiment of the present invention.

Next, an ultrasonic receiving apparatus according to a second embodiment of the present invention will be described. FIG. 8 is a block diagram showing a constitution of the ultrasonic receiving apparatus according to this embodiment.

The ultrasonic receiving apparatus according to this embodiment has a spectrometer 60 in place of the spectrometer 30 of the ultrasonic receiving apparatus shown in FIG. 1, and a mirror 61 and a mirror angle adjustment unit 62 in place of the spectrometer angle adjustment unit 31. The constitution other than the above is the same as that of the ultrasonic receiving apparatus shown in FIGS. 1 and 2.

The spectrometer 60 is constituted by, for example, a diffraction grating or a prism, and outputs the incident light in different directions according to wavelengths. In this embodiment, unlike with that in the first embodiment, the spectrometer 60 is not necessarily divided into plural spectrum-separating elements, and the angle of the spectrometer may be fixed.

The mirror 61 includes a plurality of mirror elements, angles of which are variable. These mirror elements correspond to the light beams $L_1$–$L_M$ outputted from the optical fibers $OF_1$–$OF_M$ and plural columns of the photoelectric converter 40 for calibration, respectively. Each mirror element reflects plural pieces of spectrum-separated light of the light beam spectrum-separated by the spectrometer 60 in different directions according to the incident angle, and allow them to enter the plural photoelectric conversion elements included in the respective column of the photoelectric converter 40 for calibration.

The mirror angle adjustment unit 62 adjusts the angles of the mirror elements included in the mirror 61 on the basis of the detection result of the photoelectric converter 40 for calibration, so that the spectrum-separated light having a selected wavelength of the light spectrum-separated by the spectrometer 60 may enter the photoelectric converter 50 for signal detection.

In the operation of the ultrasonic receiving apparatus according to the embodiment, the angle adjustment of the spectrum-separated light is performed as described below. First, in calibration, the light transmitted through the optical fibers connected to the respective micro areas of the ultrasonic detecting element 20 is spectrum-separated by the spectrometer 60, thereby plural pieces of spectrum-separated light are outputted in different directions according to wavelengths. These pieces of spectrum-separated light are reflected by the mirror elements included in the mirror 61, and enter the plural photoelectric conversion elements included in one column of the photoelectric converter 40 for respective wavelength components and are detected. The detection result of the photoelectric converter 40 for calibration is inputted to the mirror angle adjustment unit 62. The mirror angle adjustment unit 62 adjusts the angles of the mirror elements so that the spectrum-separated light having a wavelength, which is selected on the basis of the detection result, may enter the photoelectric converter 50 for signal detection. The principle of selection of the spectrum-separated light used for detecting ultrasonic signals is the same as that in the first embodiment of the present invention. Further, other operation of the ultrasonic receiving apparatus according to the embodiment is the same as that explained by referring to FIG. 6.

According to this embodiment, by adjusting the angles of the mirror elements, the traveling directions of the spectrum-separated light used for detecting ultrasonic waves are adjusted. Consequently, since the spectrometer can be fixed and a spectrometer unsuitable for fine angle adjustment can also be used, a wide choice of the useable spectrometer can be offered. In general, the exit angle of the spectrum-separated light is determined by characteristics of the spectrometer and its wavelength. Alternatively, the traveling directions of the plural pieces of the spectrum-separated light can also be adjusted in accordance with the arrangement of the photoelectric conversion elements in the photoelectric converter 40 by adjusting, for example, curvature of the mirror element.

As described above, in the first and second embodiments, by adjusting angles of the spectrometer or the mirror, the optical path of the spectrum-separated light is adjusted so that the spectrum-separated light having a predetermined wavelength may enter the photoelectric converter for signal detection. However, not limited to these embodiments, any constitution that provides the same function can be applied to the present invention. For example, the spectrum-separated light subjected to signal detection may be allowed to enter the photoelectric conversion element by providing means for controlling the respective positions of the plural photoelectric conversion elements included in the photoelectric converter for signal detection and changing the positions of the photoelectric conversion elements without changing the traveling direction of the spectrum-separated light outputted from the spectrometer. Alternatively, the spectrum-separated light having a selected wavelength may be allowed to enter photoelectric conversion element by using an AWG as the spectrometer to output the plural pieces of the spectrum-separated light in parallel and shifting the AWG or the photoelectric conversion elements relatively in parallel.

Figure 9:
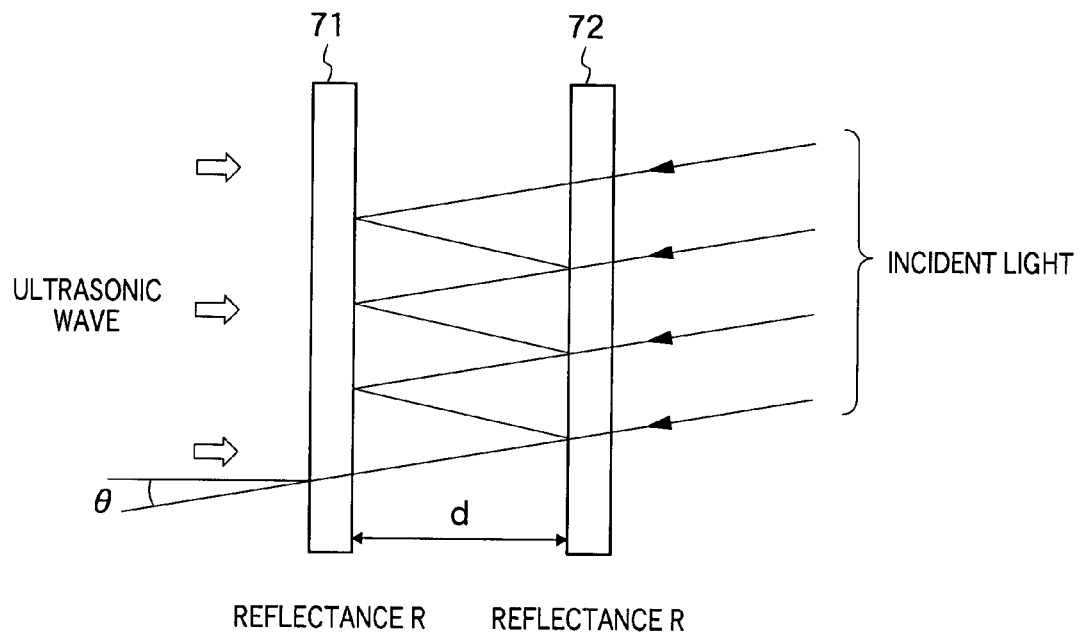
FIG. 9 is a diagram showing a part of an ultrasonic receiving apparatus according to a third embodiment of the present invention.

Next, an ultrasonic receiving apparatus according to a third embodiment of the present invention will be described by referring to FIG. 9. In the ultrasonic receiving apparatus according to this embodiment, an ultrasonic detecting element (etalon sensor) 70 shown in FIG. 9 is used in place of the ultrasonic detecting element 20 shown in FIG. 2. The constitution other than the above is the same as that described referring to FIGS. 1 and 2.

As shown in FIG. 9, a substrate 71 is a film-like substrate that is deformed by an ultrasonic wave. A substrate 72 is disposed facing to the substrate 71, and these substrates form the same structure as an etalon.

Assuming that an optical reflectance of the substrates 71 and 72 is "R", a distance between these substrates is "d", and a wavelength of the incident light is "λ", transmittance of the etalon is expressed as the following:

$$T=\{1+4R/(1-R)^2 \cdot \sin^2(\phi/2)\}^{-1} \quad (3)$$

$$\phi=2\pi/\lambda \cdot 2nd \cdot \cos\theta \quad (4)$$

Herein, "θ" is an exit angle measured from the perpendicular line with respect to the exit plane, and "n" is an arbitrary integer number. Assuming that θ=0, the following formula is held.

$$\phi=4\pi nd/\lambda \quad (5)$$

The etalon transmits the light having wavelength "λ" at an optical transmittance T, and reflects the same at an optical reflectance R=(1−T).

When an ultrasonic wave is propagated to the ultrasonic detecting element 70, since the substrate 71 is distorted and the distance "d" between the substrates 71 and 72 changes in the respective positions on the receiving surface, the reflectance with respect to the light having the wavelength "λ" changes. Therefore, similarly to that described by referring to FIG. 6, the calibration is performed, that is, the exit angle of the spectrum-separated light is adjusted so that the light having a center wavelength in a range where the optical reflectance largely changes may be detected. Then, an ultrasonic wave is applied to the substrate 71 while allowing broadband light to enter it. Thereby, it is possible to observe changes in the intensity of the reflected light according to the intensity of the ultrasonic wave at the respective positions on the receiving surface. By converting the changes in the intensity of the reflected light into the intensity of the ultrasonic wave, the intensity of the ultrasonic wave can be measured in a two-dimensional state.

Figure 10A:
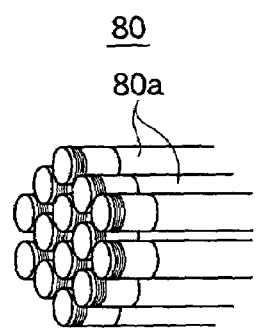
FIGS. 10A and 10B are diagrams showing parts of an ultrasonic receiving apparatus according to a fourth embodiment of the present invention.

Next, referring to FIGS. 10A and 10B, an ultrasonic receiving apparatus according to a fourth embodiment of the present invention will be described. In this embodiment, in place of the ultrasonic detecting element 20, the optical transmission path 13, and the collimating portion 14 shown in FIG. 2, a bundle fiber 80 having ultrasonic sensing portions is used as shown in FIG. 10A. The constitution other than the above is the same as that described using FIGS. 1 and 2.

Figure 10B:
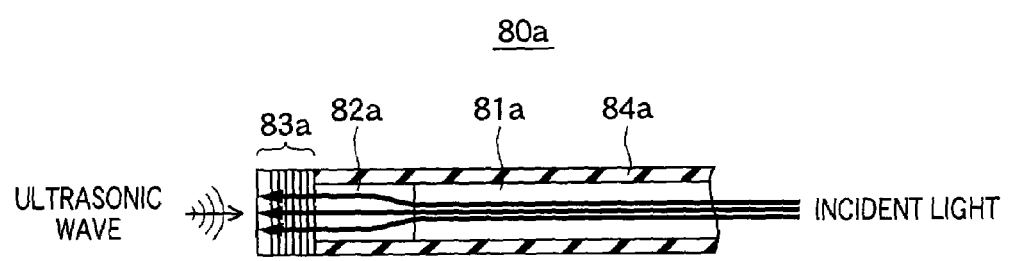

FIG. 10B shows a constitution of a fiber 80a included in the bundle fiber 80. This fiber 80a includes an optical fiber 81a and a collimator lens 82a. In this embodiment, a Selfoc lens having a length of 0.25L is used as the collimator lens 82a, similarly to that in the first embodiment. Further, the both are connected to each other by means of a fusion bond or a resinous adhesive agent including epoxy series adhesives.

A multi-layered film 83a in which two different material layers are laminated alternately is formed at one end of the collimator lens 82a. The multi-layered film 83a constitutes the Bragg grating structure and serves as the ultrasonic sensing portion. As materials of the multi-layered film 83a, for example, a combination of $SiO_2$ and titanium oxide ($Ti_2O_3$), a combination of $SiO_2$ and tantalum oxide ($Ta_2O_5$), etc. can be used. The material layer as described above has been formed on the collimator lens 82a by a method such as vacuum deposition or sputtering.

The fiber 80a is covered by a member (covering material 84a) having a low viscosity so that an ultrasonic wave may be attenuated before the ultrasonic wave having propagated to one end of the fiber 80a is reflected at the other end thereof. Further, as shown in FIG. 10B, the covering material 84a may also cover the collimator lens 82a. Thereby, since the energy loss of the ultrasonic wave propagated to the fiber 80a can be made larger, an effect as a backing portion can be improved by allowing the ultrasonic wave to attenuate earlier.

The bundle fiber 80 having the ultrasonic sensing portions is fabricated by bundling the plural fibers 80a as described above using a resinous adhesive agent including epoxy series adhesives.

In the above-described first to fourth embodiments, the ultrasonic wave detecting capability can be improved by adding a light amplifier. Referring to FIG. 11, this modification will be described.

In an ultrasonic receiving apparatus shown in FIG. 11, at least one of a light amplifier 15 and a light amplifier 16 is added to the ultrasonic receiving apparatus shown in FIG. 1. The light amplifier 15 is disposed between the collimator lens 12a and the beam separator 11, amplifies the collimated light entering from the collimator lens 12a, and outputs the light to the beam separator 11. On the other hand, the light amplifier 16 is disposed between the beam separator 11 and the spectrometer 30, amplifies the light entering from the beam separator 11, and outputs the light to the spectrometer 30.

As the light amplifier, for example, an optical fiber amplifier doped with Erbium (Er), EDFA (Er-doped optical fiber amplifier) is used. The EDFA is capable of increasing intensity of light by approximately one to two orders.

In the case where the above-described light amplifier is disposed between the light source 10 and the ultrasonic detecting element 20, the intensity of the incident light entering the ultrasonic detecting element 20 is amplified. Alternatively, in the case where the light amplifier is disposed between the ultrasonic detecting element 20 and the spectrometer 30, although the intensity of the incident light entering the ultrasonic detecting element 20 does not change, the intensity of the reflected light that enters the photoelectric converter 40 or 50 is amplified. In this case, the changes in the intensity of the reflected light that has been modulated by the received ultrasonic wave are also amplified.

In any case, since the amount of the reflected light that enters photoelectric converter 40 or 50 is increased by amplifying the intensity in the state of light, the influence of electrical noise in the photoelectric converter 40 or 50 can be reduced and the SN-ratio of the ultrasonic receiving apparatus can be improved. Further, in the case where the both of the light amplifiers are used simultaneously, the SN-ratio can be more improved.

Figure 12:
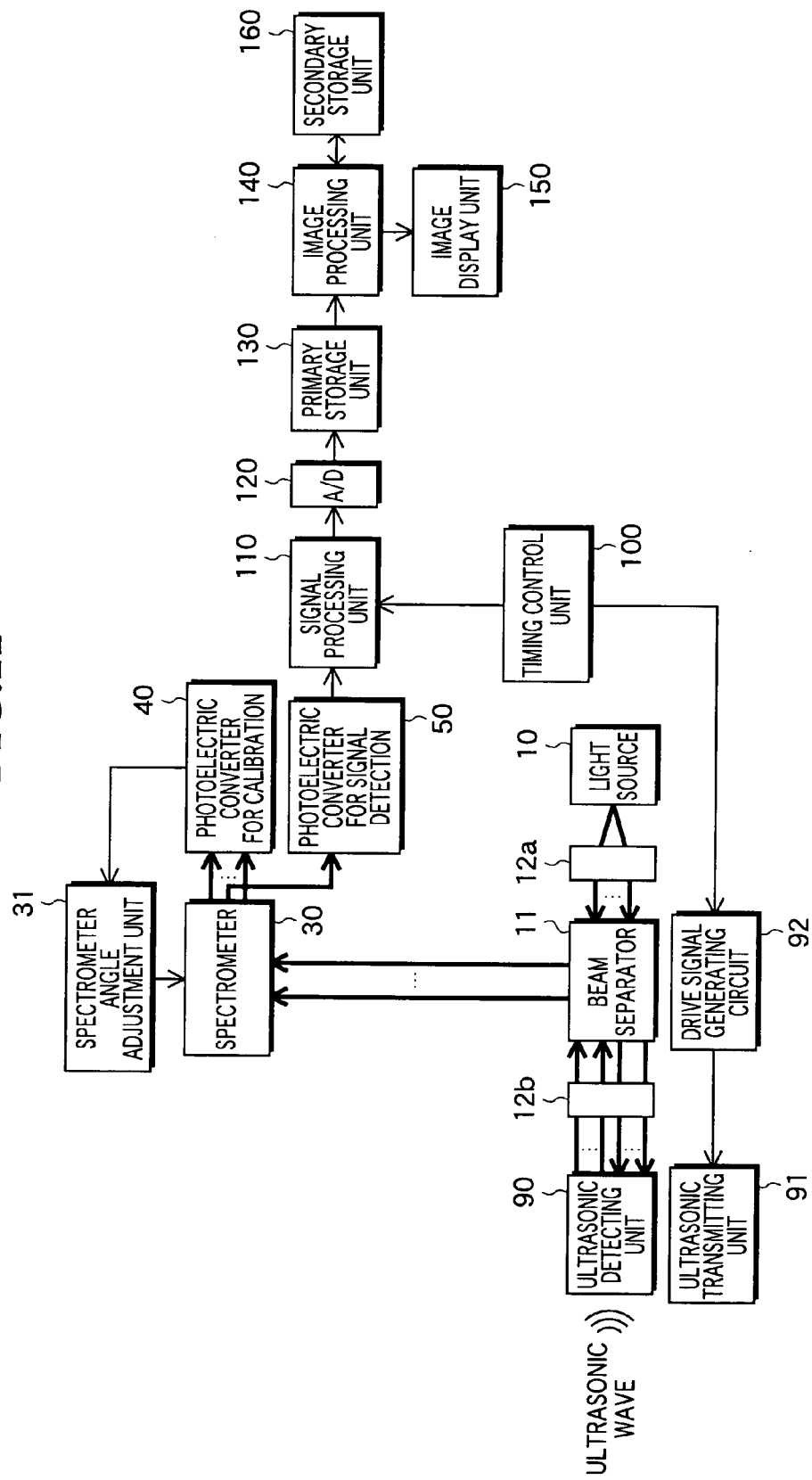
FIG. 12 is a block diagram showing a constitution of an ultrasonic imaging apparatus to which the ultrasonic receiving apparatus according to the first embodiment of the present invention is applied.

Next, an ultrasonic imaging apparatus to which the ultrasonic receiving apparatus according to the first to fourth embodiments is applied will be described. FIG. 12 is a block diagram showing a constitution of the ultrasonic imaging apparatus to which the ultrasonic receiving apparatus according to the first embodiment of the present invention is applied. Note that the ultrasonic receiving apparatus according to the second to fourth embodiments of the present invention can also be applied to the ultrasonic imaging apparatus similarly to that shown in FIG. 12.

As shown in FIG. 12, an ultrasonic detecting unit 90 includes the ultrasonic detecting element 20 described in the first embodiment of the present invention and is connected to the collimator lens 12b via the optical transmission path. The light that has been emitted from the light source and passed through the beam separator 11 enters the ultrasonic detecting unit 90. When performing the calibration, the light reflected in the ultrasonic detecting unit 90 enters the spectrometer 30 via the collimator lens 12b and the beam separator 11, and enters the photoelectric converter 40 for calibration. Thereby, the spectrum-separated light having a wavelength to be used for detecting ultrasonic waves is selected.

Further, the ultrasonic imaging apparatus also includes an ultrasonic transmitting unit 91 and a drive signal generating circuit 92. The ultrasonic transmitting unit 91 transmits an ultrasonic wave on the basis of drive signals generated by the drive signal generating circuit 92. The ultrasonic transmitting unit 91 is constituted by, for example, vibrators each of which is made by forming electrodes on a piezoelectric element. The piezoelectric element includes a material having a piezoelectric property such as piezoelectric ceramic represented by PZT (lead zirconate titanate) or macromolecule piezoelectric material represented by PVDF (polyvinylidene difluoride). Applying a voltage to the electrodes of the vibrator by transmitting an electrical pulse signal or a continuous wave electrical signal from the drive signal generating circuit 92, the piezoelectric element expands and contracts because of a piezoelectric effect. Thereby, an ultrasonic pulse or a continuous ultrasonic wave is generated from the vibrator.

The ultrasonic wave transmitted from the ultrasonic transmitting unit 91 is reflected by an object to be inspected and received by the ultrasonic detecting unit 90. Thereby, the light having entered the ultrasonic detecting unit 90 is intensity-modulated in response to the ultrasonic wave received by the ultrasonic detecting unit 90 and reflected. The reflected light enters the spectrometer 30 via the collimator lens 12b and the beam separator 11, and the spectrum-separated light having the wavelength component selected in the calibration enters the photoelectric converter 50 for signal detection.

Further, this ultrasonic imaging apparatus includes a timing control unit 100, a signal processing unit 110, an A/D converter 120, a primary storage unit 130, an image processing unit 140, a graphic display unit 150, and a secondary storage unit 160.

The detection signals respectively outputted from the plural photoelectric conversion elements included in the photoelectric converter 50 for signal detection are subjected to processing such as phase adjustment, logarithmic amplification, and demodulation in the signal processing unit 110, and further, converted into digital signals in the A/D converter 120.

The primary storage unit 130 stores data on a plurality of planes based on the converted data. The image processing unit 140 reconstitutes two-dimensional data or three-dimensional data based on the data, and performs processing such as interpolation, response modulation processing, and tone processing. The graphic display unit 150 is, for example, a display apparatus such as a CRT or an LCD, and displays images based on thus processed image data. Further, the secondary storage unit 160 stores data processed in the image processing unit 140.

The timing control unit 100 controls the drive signal generating circuit 92 to generate drive signals in predetermined timings, and controls the signal processing unit 110 to take in the detection signals outputted from the photoelectric converter 50 for signal detection after a predetermined time has passed from the time of transmission. Thus, it is possible to photo-detect the ultrasonic wave reflected from a specific depth of the object by controlling the drive signals and detection signals to limit periods for reading the detection signals.

In the above described ultrasonic imaging apparatus, the ultrasonic detecting unit 90 and the ultrasonic transmitting unit 91 may be provided separately, or an ultrasonic probe may be composed of a combination of the ultrasonic detecting unit 90 and the ultrasonic transmitting unit 91.

As described above, according to the present invention, the wavelength of the light to be used for detecting ultrasonic waves is selected from spectrum-separated light of broadband light in respective detection areas on the basis of the reflection characteristics of the ultrasonic detecting element obtained by the calibration. Therefore, in the case where the reflection characteristics change under environment such as temperature and humidity, it is possible to maintain high detection sensitivity. Further, it is similarly possible to reduce the variation of the sensitivity in respective detection areas of the ultrasonic detecting element. Consequently, the wavelength of the light of the light source and the reflection characteristics of the ultrasonic detecting element will be unnecessarily controlled and the ultrasonic receiving apparatus can be miniaturized by simplifying its constitution.

Furthermore, according the present invention, since two different photoelectric converters are used for respective purposes, optimal constitution for the respective purposes can be adopted. Specifically, the calibration is performed by using a two-dimensional photoelectric converter of low-speed processing for gaining broadband characteristics, and detection is performed by allowing thus selected spectrum-separated light only to enter a one-dimensional photoelectric converter of high-speed processing. Thereby, the cost can be reduced while maintaining the real time environment when performing ultrasonic detection. Especially, since the signal processing circuits provided in the subsequent stage of the one-dimensional photoelectric converter are necessary only for the number of photoelectric conversion elements included in the one-dimensional photoelectric converter, the cost can be drastically reduced.

The invention claimed is:

1. An ultrasonic receiving apparatus comprising:
a light source for generating broadband light;
an ultrasonic detecting element including an ultrasonic sensing portion that expands and contracts in response to a received ultrasonic wave and has optical reflectance that changes in accordance with expansion and contraction thereby performing intensity modulation on the light generated by said light source;
spectrum-separating means for spectrum-separating the light intensity-modulated by said ultrasonic detecting element;
first photo-detecting means having a plurality of photoelectric conversion elements for detecting the light spectrum-separated by said spectrum-separating means for plural wavelength components, respectively; and
second photo-detecting means for detecting a selected wavelength component included in the light spectrum-separated by said spectrum-separating means on the basis of a detection result of said first photo-detecting means.

2. The ultrasonic receiving apparatus according to claim 1, further comprising adjusting means for adjusting an optical path between said spectrum-separating means and said second photo-detecting means on the basis of the detection result of said first photo-detecting means such that the selected wavelength component included in the light spectrum-separated by said spectrum-separating means enters said second photo-detecting means.

3. The ultrasonic receiving apparatus according to claim 2, wherein said adjusting means adjusts an angle of said spectrum-separating means.

4. The ultrasonic receiving apparatus according to claim 2, further comprising:
a mirror for reflecting the light spectrum-separated by said spectrum-separating means;
wherein said adjusting means adjusts an angle of said mirror.

5. The ultrasonic receiving apparatus according to claim 1, wherein:
said ultrasonic detecting element is capable of detecting ultrasonic waves in a plurality of detection areas;
said spectrum-separating means simultaneously spectrum-separates a plurality of light beams respectively guided from the plurality of detection areas of said ultrasonic detecting element;
said first photo-detecting means detects the plurality of light beams spectrum-separated by said spectrum-separating means for respective wavelength components; and
said second photo-detecting means detects selected wavelength components respectively included in the light simultaneously spectrum-separated by said spectrum-separating means in parallel on the basis of the detection result of said first photo-detecting means.

6. The ultrasonic receiving apparatus according to claim 2, wherein:
said ultrasonic detecting element is capable of detecting ultrasonic waves in a plurality of detection areas;
said spectrum-separating means simultaneously spectrum-separates a plurality of light beams respectively guided from the plurality of detection areas of said ultrasonic detecting element;
said first photo-detecting means detects the plurality of light beams spectrum-separated by said spectrum-separating means for respective wavelength components; and
said second photo-detecting means detects selected wavelength components respectively included in the light simultaneously spectrum-separated by said spectrum-separating means in parallel on the basis of the detection result of said first photo-detecting means.

7. An ultrasonic receiving method comprising the steps of:
(a) obtaining relationship between wavelength and reflectance intensity of light in an ultrasonic detecting element including an ultrasonic sensing portion that expands and contracts in response to a received ultrasonic wave and has optical reflectance that changes in accordance with expansion and contraction thereby performing intensity modulation on entering light, by allowing the light to enter said ultrasonic detecting element, spectrum-separating the light intensity-modulated by said ultrasonic detecting element, and detecting the spectrum-separated light for plural wavelength components by using first photo-detecting means having a plurality of photoelectric conversion elements, respectively;
(b) adjusting an optical path of a selected wavelength component included in the light spectrum-separated by said spectrum-separating means on the basis of the relationship obtained at step (a) such that the selected wavelength component is outputted in a predetermined direction; and
(c) obtaining information on the ultrasonic wave received by said ultrasonic detecting element by allowing the wavelength component outputted in the predetermined direction at step (b) to enter second photo-detecting means and detecting the wavelength component.

* * * * *